United States Patent [19]

Wincott et al.

[11] Patent Number: 5,728,818
[45] Date of Patent: Mar. 17, 1998

[54] CHEMICAL LINKAGE OF RIBOZYME PROTIONS

[75] Inventors: Francine Wincott, Longmont; Nassim Usman, Boulder, both of Colo.

[73] Assignee: Ribozyme Pharmaceuticals, Inc., Boulder, Colo.

[21] Appl. No.: 585,682

[22] Filed: Jan. 16, 1996

[51] Int. Cl.$^6$ .......................... C07H 21/00; C07H 21/02; C07H 21/04

[52] U.S. Cl. ...................... 536/25.3; 536/23.1; 536/24.1; 536/24.5; 536/25.1

[58] Field of Search .............................. 435/6, 91.1, 91.3, 435/91.31, 172.1; 514/44; 536/23.1, 23.2, 24.1, 24.5, 25.3, 25.1

[56] References Cited

U.S. PATENT DOCUMENTS

| | | | |
|---|---|---|---|
| 5,298,612 | 3/1994 | Jennings et al. | 536/23.2 |
| 5,610,054 | 3/1997 | Draper et al. | 435/363 |

FOREIGN PATENT DOCUMENTS

| | | |
|---|---|---|
| 9323569 | 11/1993 | WIPO. |
| 9506731 | 3/1995 | WIPO. |
| 9531541 | 11/1995 | WIPO. |

OTHER PUBLICATIONS

Moore et al "Site Specific Modification of Pre-mRNA; The 2'-Hydroxyl Groups at the Spcice Sites", *Science* vol. 256:992-997, 1992.

Castanotto et al "Biological and Functional Aspects of Latalytic DNAs", *Critical Reviews Eukaryotic Gene Expression*, vol. 2(4):331-357, 1992.

Chowrira et al "Extensive Phosphorothioate Substitution Yields Highly Active and Nuclease Resistant Hairpin ribozymes". NAR vol. 20(11):2835-2840, 1992.

McCall et al "Minimal Sequence Requirements for Ribozyme Actiuim", DNAs vol. 89:5710-5714, 1992.

Hendry et al "Using Linkers to Investigate the Spatial Separation of the conserved Nucleotides"$A_9$ and $G_{12}$ in the Hammer Head Ribozyme. Biochimia Biophysica ACTA vol. 1219:405-412, 1994.

Cech, "Ribozymes and Their Medical Implications," *JAMA* 260:3030-3034 (1988).

Haseloff and Gerlach, "Simple RNA Enzymes with New and Highly Specific Endoribonuclease Activities," *Nature* 334:585-591 (1988).

Hui, "Synthesis and Properties of Borohydride Derivatives," *Inorg. Chem.* 19:3185-3186 (1980).

Jeffries and Symons, "A Catalytic 13-mer Ribozyme," *Nucleic Acids Research* 17:1371-1377 (1989).

Kim and Cech, "Three-dimensional model of the active site of the self-splicing rRNA precursor of *Tetrahymena*,"*Proc. Natl. Acad. Sci. USA* 84:8788-8792 (1987).

Scaringe et al., "Chemical synthesis of biologically active oligoribonucleotides using β-cyanoethyl protected ribonucleoside phosphoramidites," *Nucl Acids Res.* 18:5433-5441 (1990).

Uhlenbeck, "A Small Catalytic Oligoribonucleotide," *Nature* 328:596-600 (1987).

Usman et al., "Automated Chemical Synthesis of Long Oligoribonucleotides Using 2'-O-Silylated Ribonucleoside 3'-O-Phosphoramidites on a Controlled-Pore Glass Support: Synthesis of a 43-Nucleotide Sequence Similar to the 3'-Half Molecule of an *Escherichia coli* Formylmethoionine tRNA," *J. Am. Chem. Soc.* 109:7845-7854 (1987).

Wincott et al., "Synthesis, deprotection, analysis and purification of RNA and ribozymes," *Nucleic Acids Research* 23:2677-2684 (1995).

*Primary Examiner*—George C. Elliott
*Assistant Examiner*—Sean McGarry
*Attorney, Agent, or Firm*—Lyon & Lyon LLP

[57] ABSTRACT

Method for synthesis of an enzymatic nucleic acid by providing a 3' and a 5' portion of the enzymatic nucleic acid having independent chemically reactive groups at the 5' and 3' positions, respectively, under conditions in which a covalent bond is formed between the 3' and 5' portions by the chemically reactive groups. The bond is selected from the group consisting of, disulfide, morpholino, amide, ether, thioether, amine, a double bond, sulfonamide, ester, carbonate, and hydrazone. The bond is not the natural bond formed between a 5' phosphate group and a 3' hydroxyl group.

13 Claims, 19 Drawing Sheets

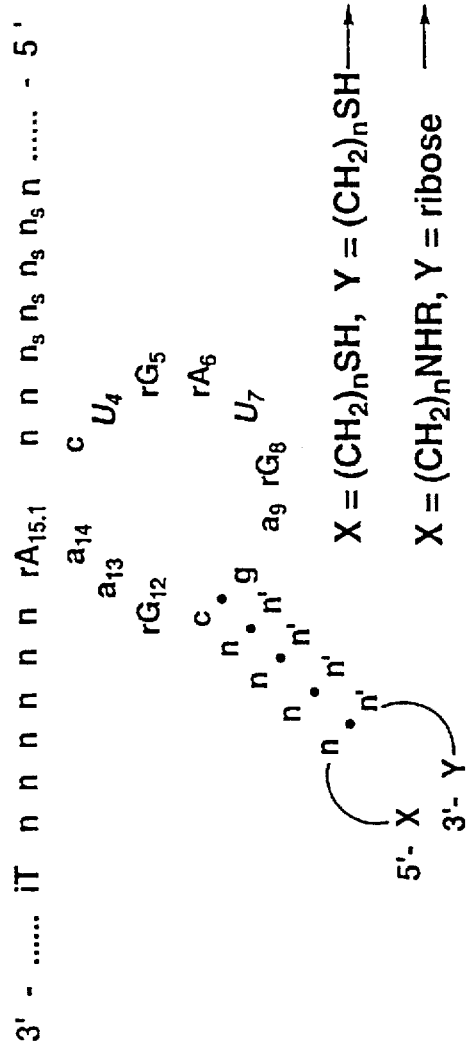

$X = (CH_2)_nSH, \quad Y = (CH_2)_nSH \longrightarrow$ disulfide $X = (CH_2)_nNHR, \quad Y =$ ribose $\longrightarrow$ morpholino $X = (CH_2)_nNHR, \quad Y = CO_2H \longrightarrow$ amide $X = (CH_2)_nX, \quad Y = (CH_2)_nOH \longrightarrow$ ether, X = halogen $X = (CH_2)_nNHR, \quad Y = CHO \longrightarrow$ amine $X = (CH_2)_nPPh_3, \quad Y = CHO \longrightarrow$ double bond $X = (CH_2)_nNHR, \quad Y = (CH_2)_nSO_2Cl \longrightarrow$ sulfonamide $X = (CH_2)_nOH, \quad Y = CO_2H \longrightarrow$ ester $X = (CH_2)_nX, \quad Y = (CH_2)_nSH \longrightarrow$ thioether, X = halogen $X = (CH_2)_nCOX, \quad Y = (CH_2)_nOH \longrightarrow$ carbonate, X = halogen $X = (CH_2)_nCOR, \quad Y = (CH_2)_nRNH \longrightarrow$ hydrazone NOTE: $(CH_2)_n$ refers to any linkage. In addition, X and Y can be interchanged.

Fig. 7

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for any
            base. The letter "H"stands for
            A, U, or C.

( x i ) SEQUENCE DESCRIPTION: SEQ ID NO:1:

NNNNUHNNNN N                                                  11

( 2 ) INFORMATION FOR SEQ ID NO:2:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for any base.

( x i ) SEQUENCE DESCRIPTION: SEQ ID NO:2:

NNNNNCUGAN GAGNNNNNNC GAAANNNN                        28

( 2 ) INFORMATION FOR SEQ ID NO:3:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for any
           base. The letter "Y"stands for
           U or C. The letter "H"stands
           for A, U, or C.

( x i ) SEQUENCE DESCRIPTION: SEQ ID NO:3:

NNNNNNN Y NG H Y NNN                                      15

( 2 ) INFORMATION FOR SEQ ID NO:4:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for any
           base. The letter "H"stands for
           A, U, or C.

( x i ) SEQUENCE DESCRIPTION: SEQ ID NO:4:

NNNNGAAGNN NNNNNNNNA AAHANNNNNN NACAUUACNN NNNNNNN        47

( 2 ) INFORMATION FOR SEQ ID NO:5:

( i ) SEQUENCE CHARACTERISTICS:
  ( A ) LENGTH: 85 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:5:

| | | | | | | |
|---|---|---|---|---|---|---|
| UGGCCGGCAU | GGUCCCAGCC | UCCUCGCUGG | CGCCGGCUGG | GCAACAUUCC | GAGGGGACCG | 60 |
| UCCCCUCGGU | AAUGGCGAAU | GGGAC | | | | 85 |

( 2 ) INFORMATION FOR SEQ ID NO:6:

( i ) SEQUENCE CHARACTERISTICS:
  ( A ) LENGTH: 176 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:6:

| | | | | | | |
|---|---|---|---|---|---|---|
| GGGAAAGCUU | GCGAAGGGCG | UCGUCGCCCC | GAGCGGUAGU | AAGCAGGGAA | CUCACCUCCA | 60 |
| AUUUCAGUAC | UGAAAUUGUC | GUAGCAGUUG | ACUACUGUUA | UGUGAUUGGU | AGAGGCUAAG | 120 |
| UGACGGUAUU | GGCGUAAGUC | AGUAUUGCAG | CACAGCACAA | GCCCGCUUGC | GAGAAU | 176 |

( 2 ) INFORMATION FOR SEQ ID NO:7:

( i ) SEQUENCE CHARACTERISTICS:
  ( A ) LENGTH: 32 base pairs
  ( B ) TYPE: nucleic acid
  ( C ) STRANDEDNESS: single
  ( D ) TOPOLOGY: linear ( i x ) FEATURE:
  ( D ) OTHER INFORMATION: The letter "N" stands for any base.

( x i ) SEQUENCE DESCRIPTION: SEQ ID NO:7:

NNNNNNCUG AUGAGNNNNN NCGAAANNNN NN                                          32

( 2 ) INFORMATION FOR SEQ ID NO:8:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( i x ) FEATURE:
  ( D ) OTHER INFORMATION: The letter "N" stands for any base.

( x i ) SEQUENCE DESCRIPTION: SEQ ID NO:8:

NNNNNNNCUG AUGAGNNN                                                         18

( 2 ) INFORMATION FOR SEQ ID NO:9:

( i ) SEQUENCE CHARACTERISTICS:
  ( A ) LENGTH: 14 base pairs
  ( B ) TYPE: nucleic acid
  ( C ) STRANDEDNESS: single
  ( D ) TOPOLOGY: linear ( i x ) FEATURE:
  ( D ) OTHER INFORMATION: The letter "N" stands for any base.

( x i ) SEQUENCE DESCRIPTION: SEQ ID NO:9:

NNNCGAAANN NNNN                                                             14

( 2 ) INFORMATION FOR SEQ ID NO:10:

( i ) SEQUENCE CHARACTERISTICS:
 ( A ) LENGTH: 16 base pairs
 ( B ) TYPE: nucleic acid
 ( C ) STRANDEDNESS: single
 ( D ) TOPOLOGY: linear ( i x ) FEATURE:
 ( D ) OTHER INFORMATION: The letter "N" stands for any base.

( x i ) SEQUENCE DESCRIPTION: SEQ ID NO:10:

NNNNCGAAAN NNNNNT 16

( 2 ) INFORMATION FOR SEQ ID NO:11:

( i ) SEQUENCE CHARACTERISTICS:
 ( A ) LENGTH: 19 base pairs
 ( B ) TYPE: nucleic acid
 ( C ) STRANDEDNESS: single
 ( D ) TOPOLOGY: linear ( i x ) FEATURE:
 ( D ) OTHER INFORMATION: The letter "N" stands for any base.

( x i ) SEQUENCE DESCRIPTION: SEQ ID NO:11:

NNNNNNNCUG AUGAGNNNN 19

( 2 ) INFORMATION FOR SEQ ID NO:12:

( i ) SEQUENCE CHARACTERISTICS:
 ( A ) LENGTH: 34 base pairs
 ( B ) TYPE: nucleic acid
 ( C ) STRANDEDNESS: single
 ( D ) TOPOLOGY: linear ( i x ) FEATURE:
 ( D ) OTHER INFORMATION: The letter "N" stands for any base.

( x i ) SEQUENCE DESCRIPTION: SEQ ID NO:12:

GUUUCCCUG AUGAGNNNNN NNNCGAAAUU CUCC 34

( 2 ) INFORMATION FOR SEQ ID NO:13:

( i ) SEQUENCE CHARACTERISTICS:
 ( A ) LENGTH: 34 base pairs
 ( B ) TYPE: nucleic acid
 ( C ) STRANDEDNESS: single
 ( D ) TOPOLOGY: linear ( i x ) FEATURE:
 ( D ) OTHER INFORMATION: The letter "N" stands for any base.

( x i ) SEQUENCE DESCRIPTION: SEQ ID NO:13:

GUUUCCCUG AUGAGNNNNN NNNCGAAAUU CUCC 34

( 2 ) INFORMATION FOR SEQ ID NO:14:

( i ) SEQUENCE CHARACTERISTICS:
 ( A ) LENGTH: 15 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:14:

GGAGAAUUGG AAAAC 15

( 2 ) INFORMATION FOR SEQ ID NO:15:

( i ) SEQUENCE CHARACTERISTICS:
 ( A ) LENGTH: 34 base pairs ( B ) TYPE: nucleic acid
( C ) STRANDEDNESS: single
( D ) TOPOLOGY: linear ( x i ) SEQUENCE DESCRIPTION: SEQ ID NO:15:

GUUUUCCCUG AUGAGCACCG GUGCGAAAUU CUCC      3 4

CHEMICAL LINKAGE OF RIBOZYME PROTIONS

This application is a Continuation-in-part of Wincott and Usman, U.S. Ser. No. 60/000,974 all of which is incorporated by reference herein (including drawings).

This invention relates to methods for synthesis of enzymatic nucleic acid molecules.

BACKGROUND OF THE INVENTION

Ribozymes are nucleic acid molecules having an enzymatic activity which is able to repeatedly cleave other separate RNA molecules in a nucleotide base sequence specific manner. Such enzymatic RNA molecules can be targeted to virtually any RNA transcript, and efficient cleavage achieved in vitro. Kim et al., 84 *Proc. Natl. Acad. Sci. USA* 8788, 1987; Haseloff and Gerlach, 334 *Nature* 585, 1988; Cech, 260 *JAMA* 3030, 1988; and Jefferies et al., 17 *Nucleic Acids Research* 1371, 1989.

Ribozymes act by first binding to a target RNA. Such binding occurs through the target RNA binding portion of a ribozyme which is held in close proximity to an enzymatic portion of the RNA which acts to cleave the target RNA. Thus, the ribozyme first recognizes and then binds a target RNA through complementary base-pairing, and once bound to the correct site, acts enzymatically to cut the target RNA. Strategic cleavage of such a target RNA will destroy its ability to direct synthesis of an encoded protein. After a ribozyme has bound and cleaved its RNA target it is released from that RNA to search for another target and can repeatedly bind and cleave new targets.

By "complementarity" is meant a nucleic acid that can form hydrogen bond(s) with other RNA sequences by either traditional Watson-Crick or other non-traditional types (for example, Hoogsteen type) of base-paired interactions.

Six basic varieties of naturally-occurring enzymatic RNAs are known presently. Each can catalyze the hydrolysis of RNA phosphodiester bonds in trans (and thus can cleave other RNA molecules) under physiological conditions. Table I summarizes some of the characteristics of these ribozymes. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The general structure of various ribozyme motifs is described by Draper et al. WO 93/23569, at pages 3–4 and in Usman et al., 95/06731 at pages 1–7 hereby incorporated by reference herein in its entirety (including drawings). Other motifs are also known in the art.

The enzymatic nature of a ribozyme is advantageous over other technologies, such as antisense technology (where a nucleic acid molecule simply binds to a nucleic acid target to block its translation) since the effective concentration of ribozyme necessary to effect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base pairing. Thus, it is thought that the specificity of action of a ribozyme is greater than that of antisense oligonucleotide binding the same RNA site.

Jennings et al., U.S. Pat. No. 5,298,612 describe the use of non-nucleotides to assemble a hammerhead ribozyme lacking a stem II portion.

Draper et al., WO 93/23569 (PCT/US93/04020) describes synthesis of ribozymes in two parts in order to aid in the synthetic process (see, e.g., pages 173–174).

Usman et al., WO 95/06731, describe enzymatic nucleic acid molecules having non-nucleotides within their structure. Such non-nucleotides can be used in place of nucleotides to allow formation of an enzymatic nucleic acid.

SUMMARY OF THE INVENTION

This invention relates to improved methods for synthesis of enzymatic nucleic acids and, in particular, hammerhead and hairpin motif ribozymes. This invention is advantageous over iterative chemical synthesis of ribozymes since the yield of the final ribozyme can be significantly increased. Rather than synthesizing, for example, a 37mer hammerhead ribozyme, two partial ribozyme portions, e.g., a 20mer and a 17mer, can be synthesized in significantly higher yield, and the two reacted together to form the desired enzymatic nucleic acid.

Referring to FIG. 6, the strategy involved is shown for a hammerhead ribozyme where each n or n' is independently any desired nucleotide or non-nucleotide, each filled-in circle represents pairing between bases or other entities, and the solid line represents a covalent bond. Within the structure each n and n' may be a ribonucleotide, a 2'-methoxy-substituted nucleotide, or any other type of nucleotide which does not significantly affect the desired enzymatic activity of the final product (see Usman et al., supra). In the particular embodiment shown, which is not limiting in this invention, five ribonucleotides are provided at rG5, rA6, rG8, rG12, and rA15.1. U4 and U7 may be abasic (i.e., lacking the uridine moiety) or may be ribonucleotides, 2'-methoxy substituted nucleotides, or other such nucleotides. a9, a13, and a14 are preferably 2'-methoxy or may have other substituents. The synthesis of this hammerhead ribozyme is performed by synthesizing a 3' and a 5' portion as shown in a lower part of FIG. 6. Each 5' and 3' portion has a chemically reactive group X and Y, respectively. Non-limiting examples of such chemically reactive groups are provided in FIG. 7. These groups undergo chemical reactions to provide the bonds shown in FIG. 7. Thus, the X and Y can be used, in various combinations, in this invention to form a chemical linkage between two ribozyme portions.

Thus, in a first aspect the invention features a method for synthesis of an enzymatically active nucleic acid (as defined by Draper, supra) by providing a 3' and a 5' portion of that nucleic acid, each having independently chemically reactive groups at the 5' and 3' positions, respectively. The reaction is performed under conditions in which a covalent bond is formed between the 3' and 5' portions by those chemically reactive groups. The bond formed can be, but is not limited to, either a disulfide, morpholino, amide, ether, thioether, amine, a double bond, a sulfonamide, carbonate, hydrazone or ester bond. The bond is not the natural bond formed between a 5' phosphate group and a 3' hydroxyl group which is made during normal synthesis of an oligonucleotide. In other embodiments, more than two portions can be linked together using pairs of X and Y groups which allow proper formation of the ribozyme.

By "chemically reactive group" is simply meant a group which can react with another group to form the desired bonds. These bonds may be formed under any conditions which will not significantly affect the structure of the resulting enzymatic nucleic acid. Those in the art will recognize that suitable protecting groups can be provided on the ribozyme portions.

In preferred embodiments the nucleic acid has a hammerhead motif and the 3' and 5' portions each have chemically reactive groups in or immediately adjacent to the stem II region (see FIG. 1). The stem II region is evident in FIG. 1 between the bases termed a9 and rG12. The C and G within this stem defines the end of the stem II region. Thus, any of the n or n' moieties within the stem II region can be provided with a chemically reactive group. As is evident from this structure, the chemically reactive groups need not be provided in the solid line portion but can be provided at any of the n or n'. In this way the length of each of the 5' and 3' portions can vary by several bases.

In other preferred embodiments, the chemically reactive group can be, but is not limited to, $(CH_2)_n SH$; $(CH_2)_n NHR$; $(CH_2)_n X$; ribose; COOH; $(CH_2)_n PPh_3$; $(CH_2)_n SO_2Cl$; $(CH_2)_n COR$; $(CH_2)_n RNH$ or $(CH_2)_n OH$, where, $CH_2$ can be replaced by another group which forms linking chain containing various atoms including, but not limited to $CH_2$, such as methylenes, ether, ethylene glycol, thioethers, double bonds, aromatic groups and others; each n independently is an integer from 0 to 10 inclusive and may be the same or different; each R independently is a proton or an alkyl, alkenyl and other functional groups or conjugates such as peptides, steroids, hoemones, lipids, nucleic acid sequences and others that provides nuclease resistance, improved cell association, improved cellular uptake or interacellular localization. X is halogen, and Ph represents a phenyl ring.

Specifically, an "alkyl" group refers to a saturated aliphatic hydrocarbon, including straight-chain, branched-chain, and cyclic alkyl groups. Preferably, the alkyl group has 1 to 12 carbons. More preferably it is a lower alkyl of from 1 to 7 carbons, more preferably 1 to 4 carbons. The alkyl group may be substituted or unsubstituted. When substituted the substituted group(s) is preferably, hydroxyl, cyano, alkoxy, =O, =S, $NO_2$ or $N(CH_3)_2$, amino, or SH. The term also includes alkenyl groups which are unsaturated hydrocarbon groups containing at least one carbon-carbon double bond, including straight-chain, branched-chain, and cyclic groups. Preferably, the alkenyl group has 1 to 12 carbons. More preferably it is a lower alkenyl of from 1 to 7 carbons, more preferably 1 to 4 carbons. The alkenyl group may be substituted or unsubstituted. When substituted the substituted group(s) is preferably, hydroxyl, cyano, alkoxy, =O, =S, $NO_2$, halogen, $N(CH_3)_2$, amino, or SH. The term "alkyl" also includes alkynyl groups which have an unsaturated hydrocarbon group containing at least one carbon-carbon triple bond, including straight-chain, branched-chain, and cyclic groups. Preferably, the alkynyl group has 1 to 12 carbons. More preferably it is a lower alkynyl of from 1 to 7 carbons, more preferably 1 to 4 carbons. The alkynyl group may be substituted or unsubstituted. When substituted the substituted group(s) is preferably, hydroxyl, cyano, alkoxy, =O, =S, $NO_2$ or $N(CH_3)_2$, amino or SH.

Such alkyl groups may also include aryl, alkylaryl, carbocyclic aryl, heterocyclic aryl, amide and ester groups. An "aryl" group refers to an aromatic group which has at least one ring having a conjugated π electron system and includes carbocyclic aryl, heterocyclic aryl and biaryl groups, all of which may be optionally substituted. The preferred substituent(s) of aryl groups are halogen, trihalomethyl, hydroxyl, SH, OH, cyano, alkoxy, alkyl, alkenyl, alkynyl, and amino groups. An "alkylaryl" group refers to an alkyl group (as described above) covalently joined to an aryl group (as described above). Carbocyclic aryl groups are groups wherein the ring atoms on the aromatic ring are all carbon atoms. The carbon atoms are optionally substituted. Heterocyclic aryl groups are groups having from 1 to 3 heteroatoms as ring atoms in the aromatic ring and the remainder of the ring atoms are carbon atoms. Suitable heteroatoms include oxygen, sulfur, and nitrogen, and include furanyl, thienyl, pyridyl, pyrrolyl, N-lower alkyl pyrrolo, pyrimidyl, pyrazinyl, imidazolyl and the like, all optionally substituted. An "amide" refers to an —C(O)—NH—R, where R is either alkyl, aryl, alkylaryl or hydrogen. An "ester" refers to an —C(O)—OR', where R is either alkyl, aryl, alkylaryl or hydrogen.

In yet other preferred embodiments, the conditions include provision of $NaIO_4$ in contact with the ribose, and subsequent provision of a reducing group such as $NaBH_4$ or $NaCNBH_3$; or the conditions include provision of a coupling reagent.

In a second related aspect, the invention features a mixture of the 5' and 3' portions of the enzymatically active nucleic acids having the 3' and 5' chemically reactive groups noted above.

Those in the art will recognize that while examples are provided of half ribozymes it is possible to provide ribozymes in 3 or more portions. For example, the hairpin ribozyme may be synthesized by inclusion of chemically reactive groups in helix IV and in other helices which are not critical to the enzymatic activity of the nucleic acid.

Other features and advantages of the invention will be apparent from the following description of the preferred embodiments thereof, and from the claims.

DESCRIPTION OF THE PREFERRED EMBODIMENTS

The drawings will first briefly be described.

DRAWINGS

FIG. 1 is a diagrammatic representation of the hammerhead ribozyme domain known in the art. Stem II can be ≧2 base-pair long. Each N is independently any base or nonnucleotide as used herein.

Figure 2A:
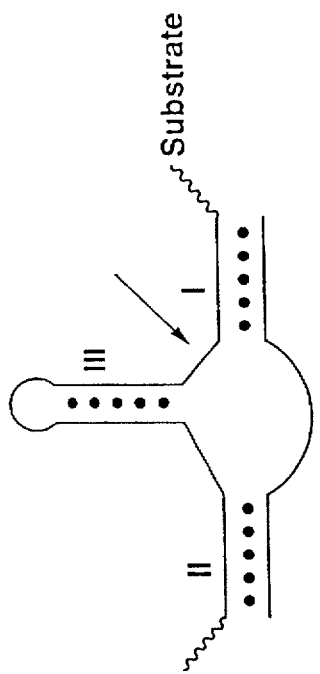
FIG. 2a is a diagrammatic representation of the hammerhead ribozyme domain known in the art.
Figure 2C:
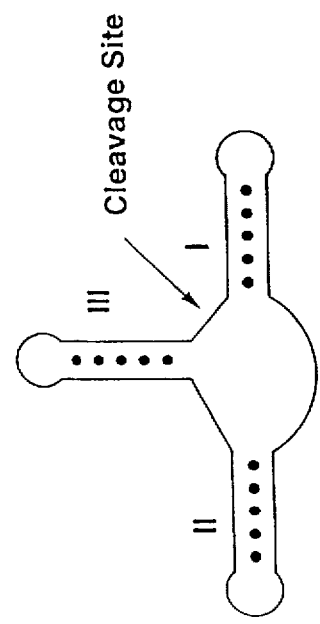
FIG. 2c is a similar diagram showing the hammerhead divided by Haseloff and Gerlach (1988, *Nature*, 334, 585–591) into two portions.
Figure 2B:
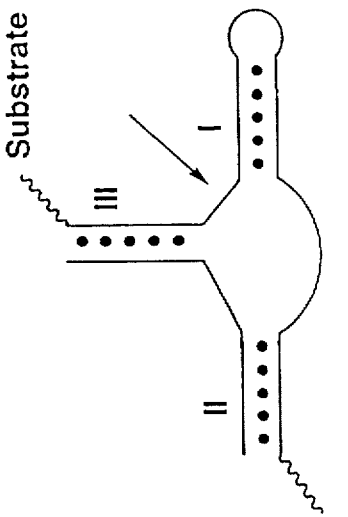
FIG. 2b is a diagrammatic representation of the hammerhead ribozyme as divided by Uhlenbeck (1987, *Nature*, 327, 596–600) into a substrate and enzyme portion.
Figure 2D:
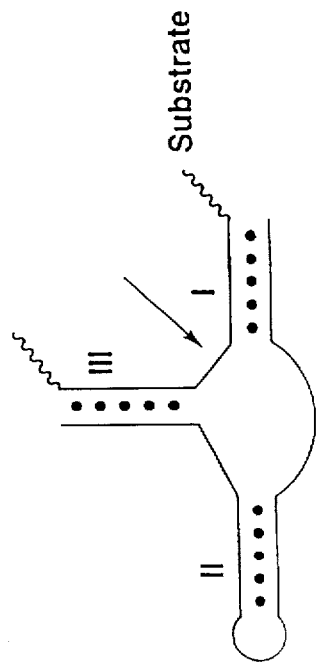

FIG. 2d is a similar diagram showing the hammerhead divided by Jeffries and Symons (1989, *Nucl. Acids. Res.*, 17, 1371–1371)into two portions.

Figure 3:
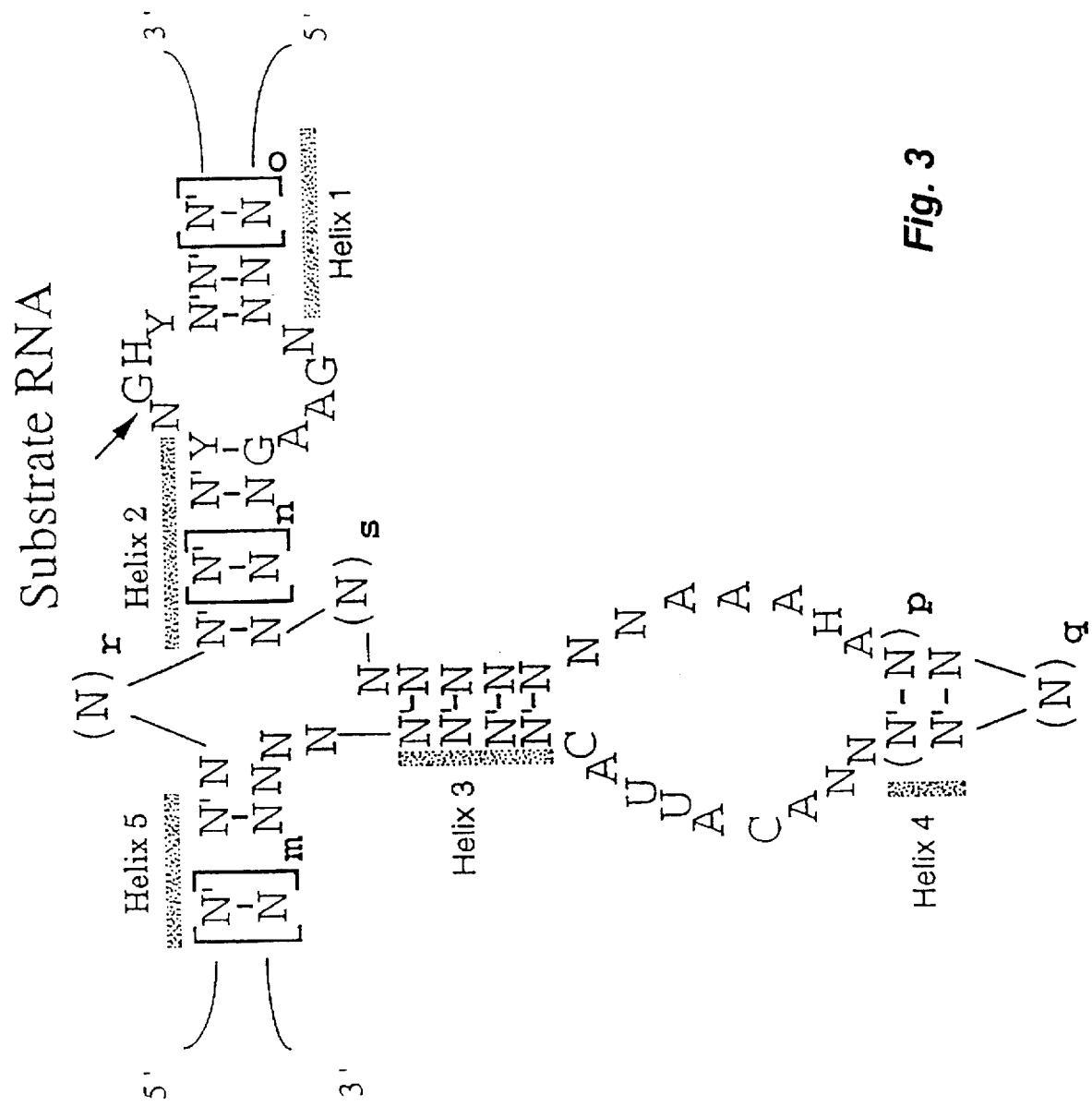

FIG. 3 is a diagrammatic representation of the general structure of a hairpin ribozyme. Helix 2 (H2) is provided with at least 4 base pairs (i.e., n is 1, 2, 3 or 4) and helix 5 can be optionally provided of length 2 or more bases (preferably 3–20 bases, i.e., m is from 1–20 or more). Helix 2 and helix 5 may be covalently linked by one or more bases (i.e., r is ≧1 base). Helix 1, 4 or 5 may also be extended by 2 or more base pairs (e.g., 4–20 base pairs) to stabilize the ribozyme structure, and preferably is a protein binding site. In each instance, each N and N' independently is any normal or modified base and each dash represents a potential base-pairing interaction. These nucleotides may be modified at the sugar, base or phosphate. Complete base-pairing is not required in the helices, but is preferred. Helix 1 and 4 can be of any size (i.e., o and p is each independently from 0 to any number, e.g., 20) as long as some base-pairing is maintained. Essential bases are shown as specific bases in the structure, but those in the art will recognize that one or more may be modified chemically (abasic, base, sugar and/or phosphate modifications) or replaced with another base without significant effect. Helix 4 can be formed from two separate molecules, i.e., without a connecting loop. The connecting loop when present may be a ribonucleotide with or without modifications to its base, sugar or phosphate. "q" is ≧2 bases. The connecting loop can also be replaced with a non-nucleotide linker molecule. H, refers to bases A, U or C. Y refers to pyrimidine bases. "____" refers to a covalent bond.

Figure 4:
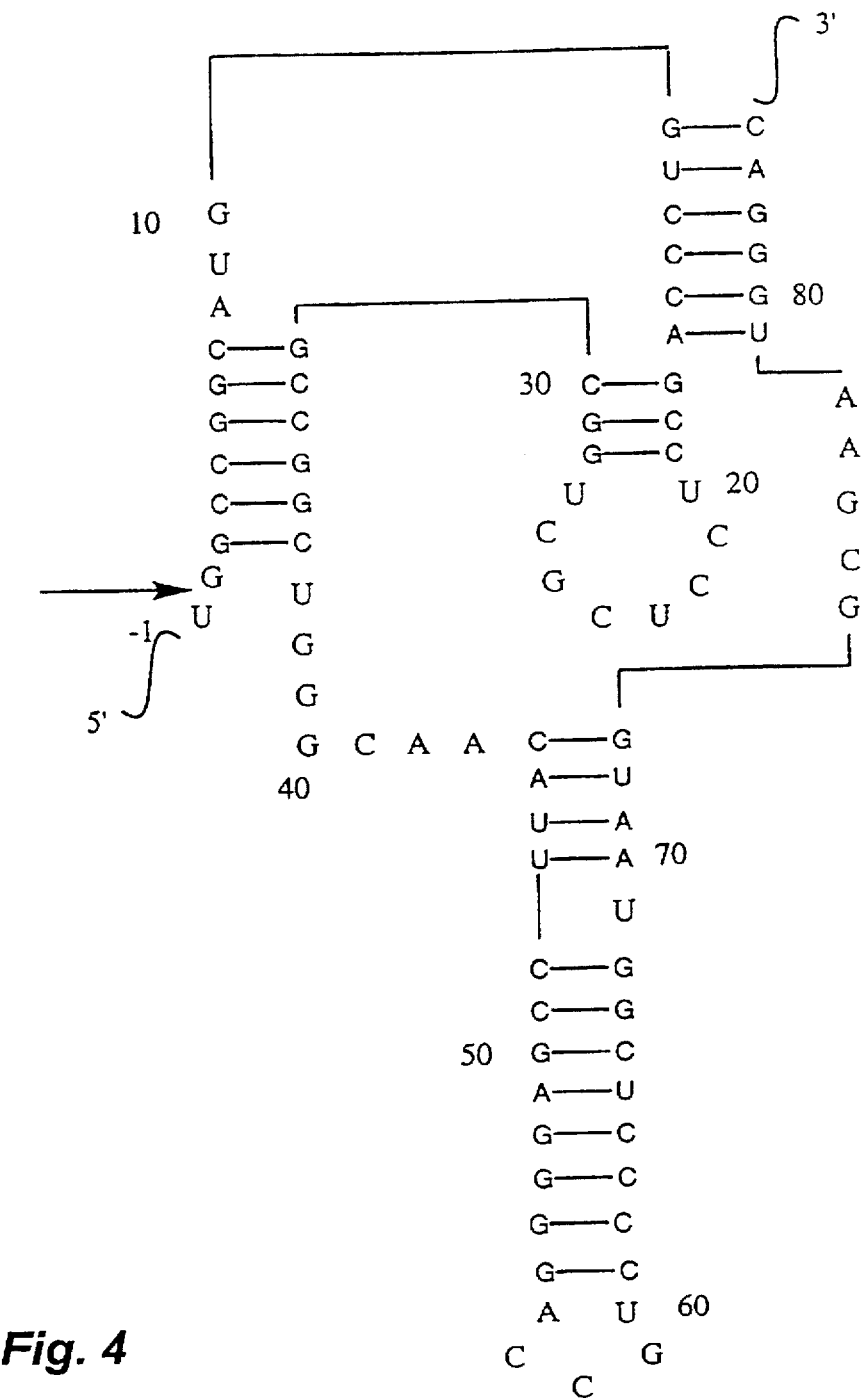

FIG. 4 is a representation of the general structure of the hepatitis delta virus ribozyme domain known in the art.

Figure 5:
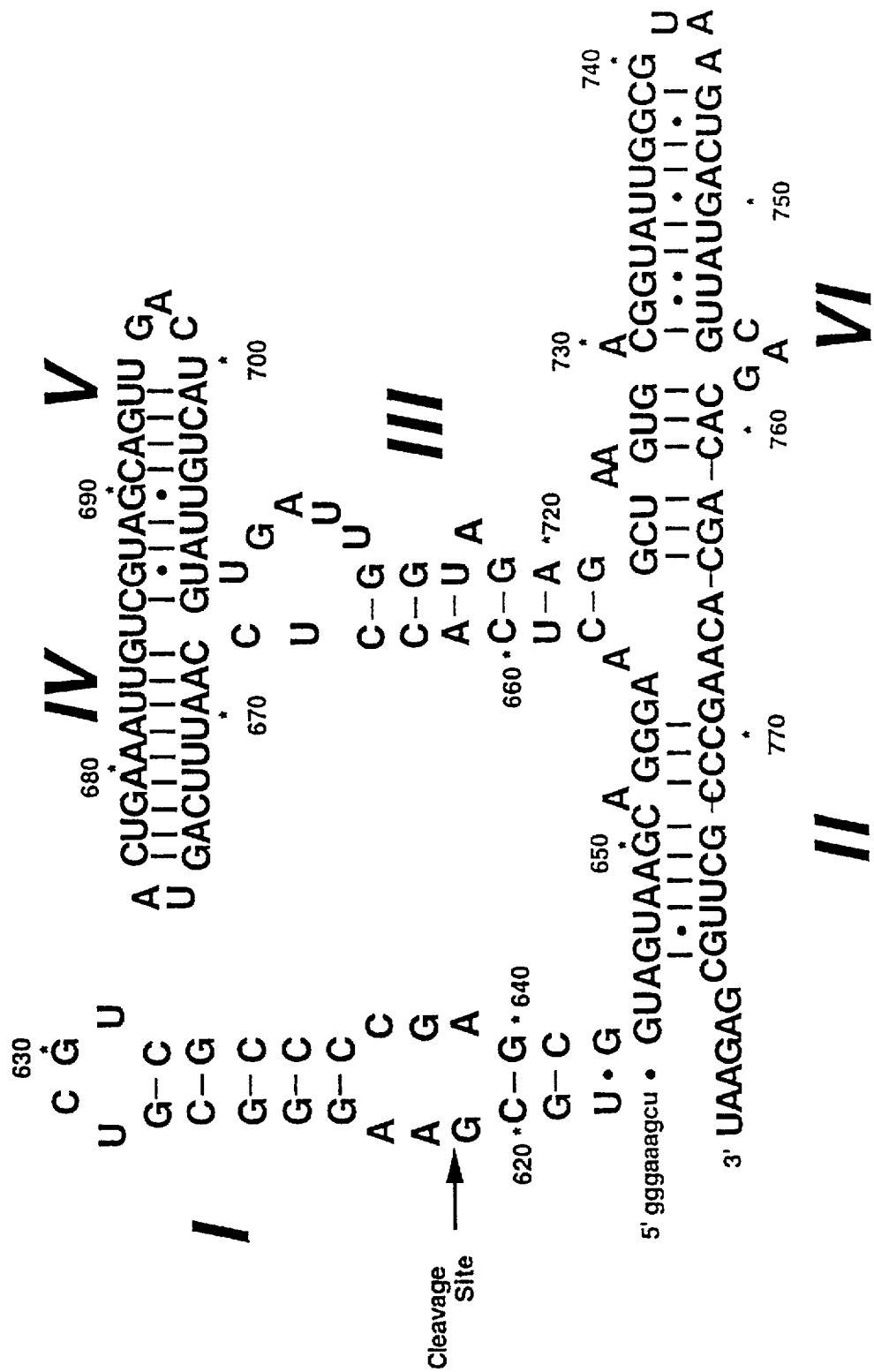

FIG. 5 is a representation of the general structure of the self-cleaving VS RNA ribozyme domain.

Figure 6:
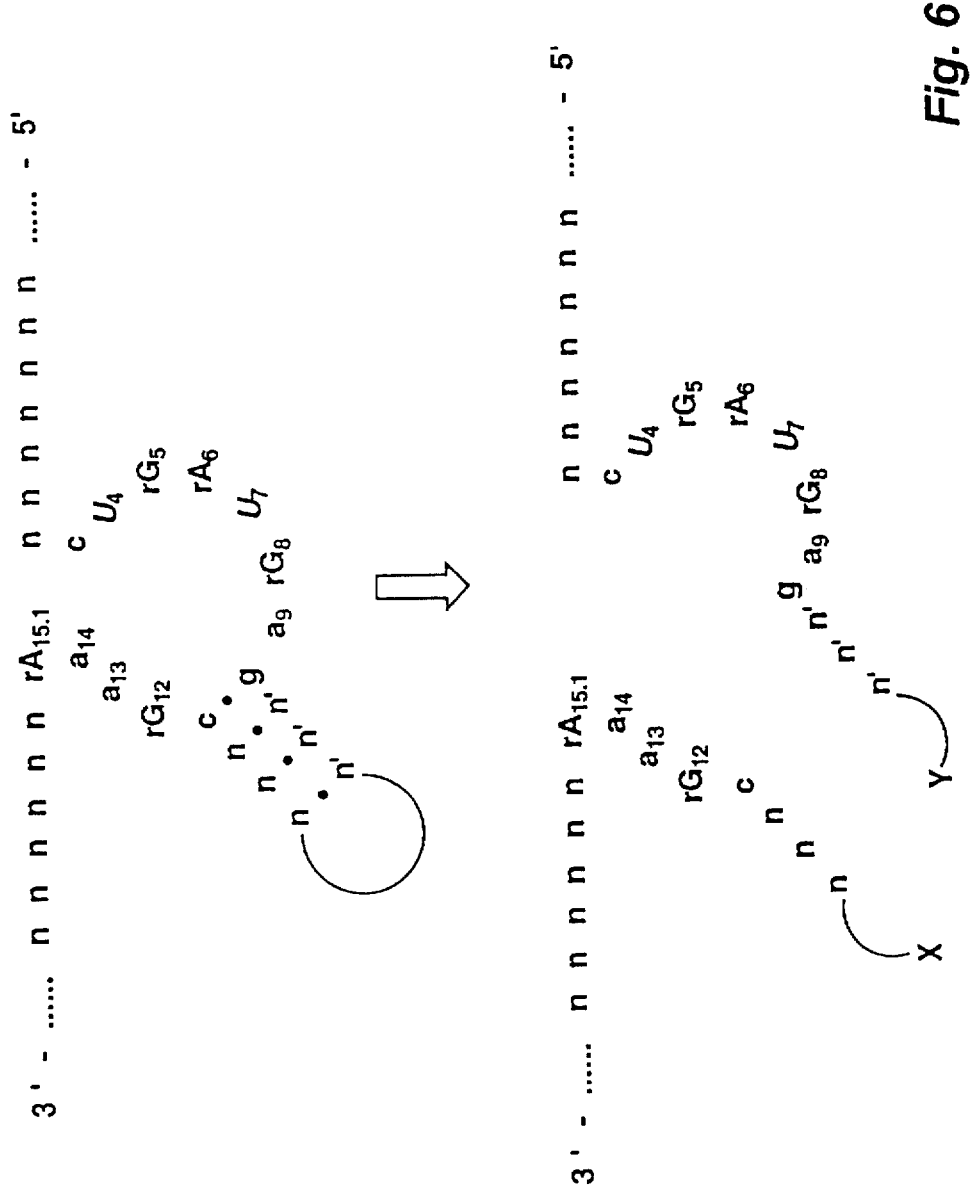

FIG. 6 shows a strategy used in synthesizing a hammerhead ribozyme from two halves. X and Y represent reactive moieties that can undergo a chemical reaction to form a covalent bond (represented by the solid curved line).

FIG. 7 shows various non-limiting examples of reactive moieties that can be placed in the nascent loop region to form a covalent bond to provide a full-length ribozyme. $CH_2$ can be any linking chain as described above including groups such as methylenes, ether, ethylene glycol, thioethers, double bonds, aromatic groups and others; each n independently is an integer from 0 to 10 inclusive and may be the same or different; each R independently is a proton or an alkyl, alkenyl and other functional groups or conjugates such as peptides, steroids, hoemones, lipids, nucleic acid sequences and others that provides nuclease resistance, improved cell association, improved cellular uptake or interacellular localization.

Figure 8A:
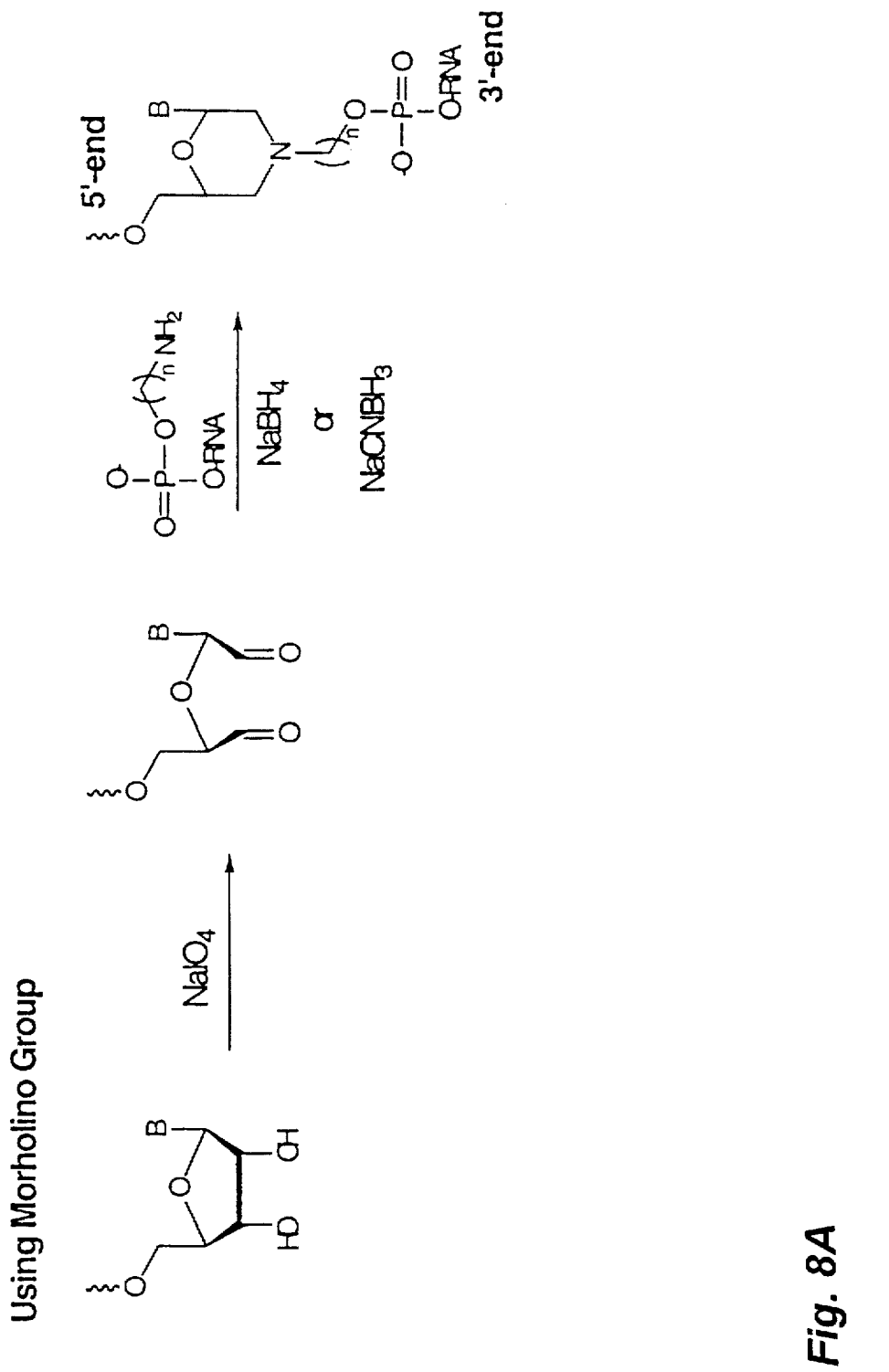
Figure 8B:
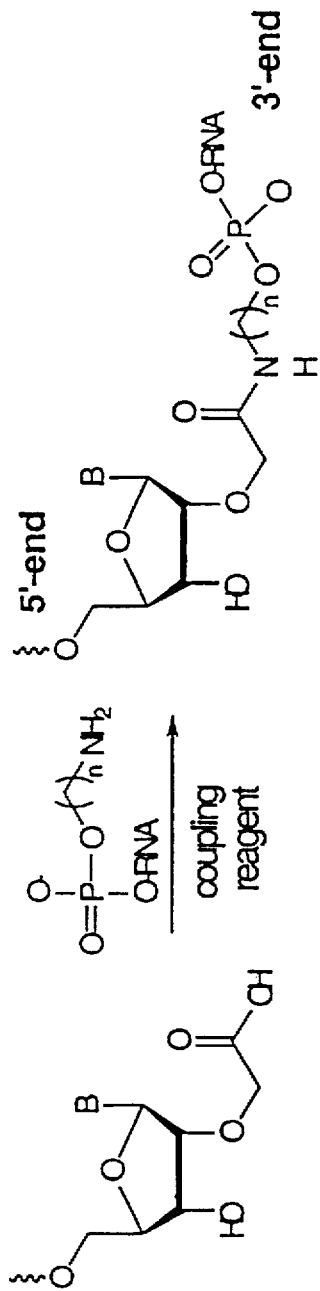

FIG. 8 shows non-limiting examples of covalent bonds that can be formed to provide the full length ribozyme. The morpholino group arises from reductive reaction of a dialdehyde, which arises from oxidative cleavage of a ribose at the 3'-end of one half ribozyme with an amine at the 5'-end of the half ribozyme. The amide bond is produced when an acid at the 3'-end of one half ribozyme is coupled to an amine at the 5'-end of the other half ribozyme.

Figure 9A:
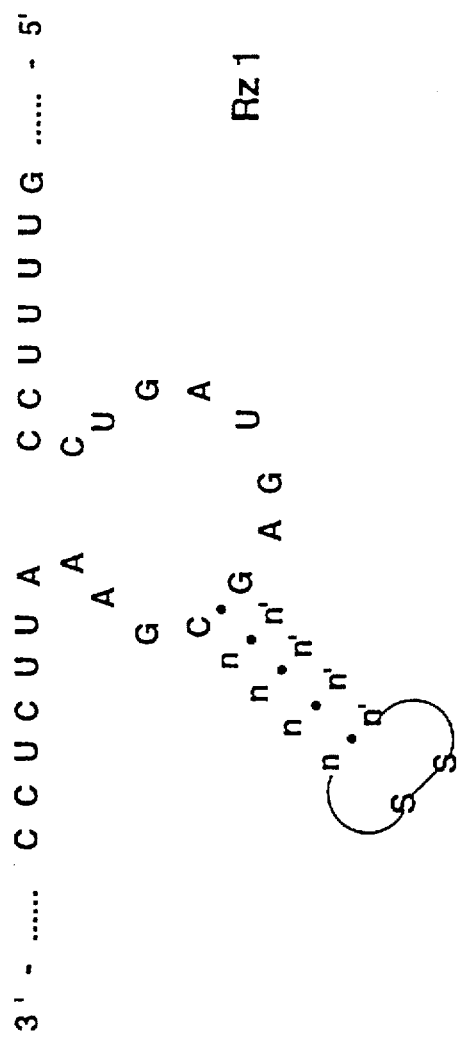
Figure 9B:
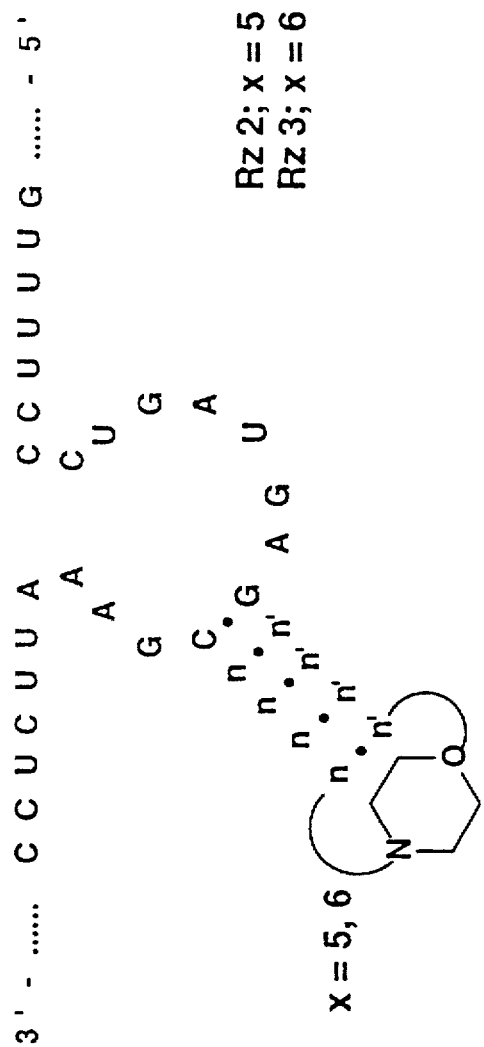

FIG. 9 shows non-limiting examples of three ribozymes that were synthesized from coupling reactions of two halves. All three were targeted to the 575 site of c-myb RNA. Rz 1 was formed from the reaction of two thiols to provide the disulfide linked ribozyme. Rz 2 and Rz 3 were formed using the morpholino reaction. Rz 2 contains a five atom spacer linking the terminal amine to the 5'-end of the half ribozyme. Rz 3 contains a six carbon spacer linking the terminal amine to the 5'-end of the half ribozyme.

Figure 10:
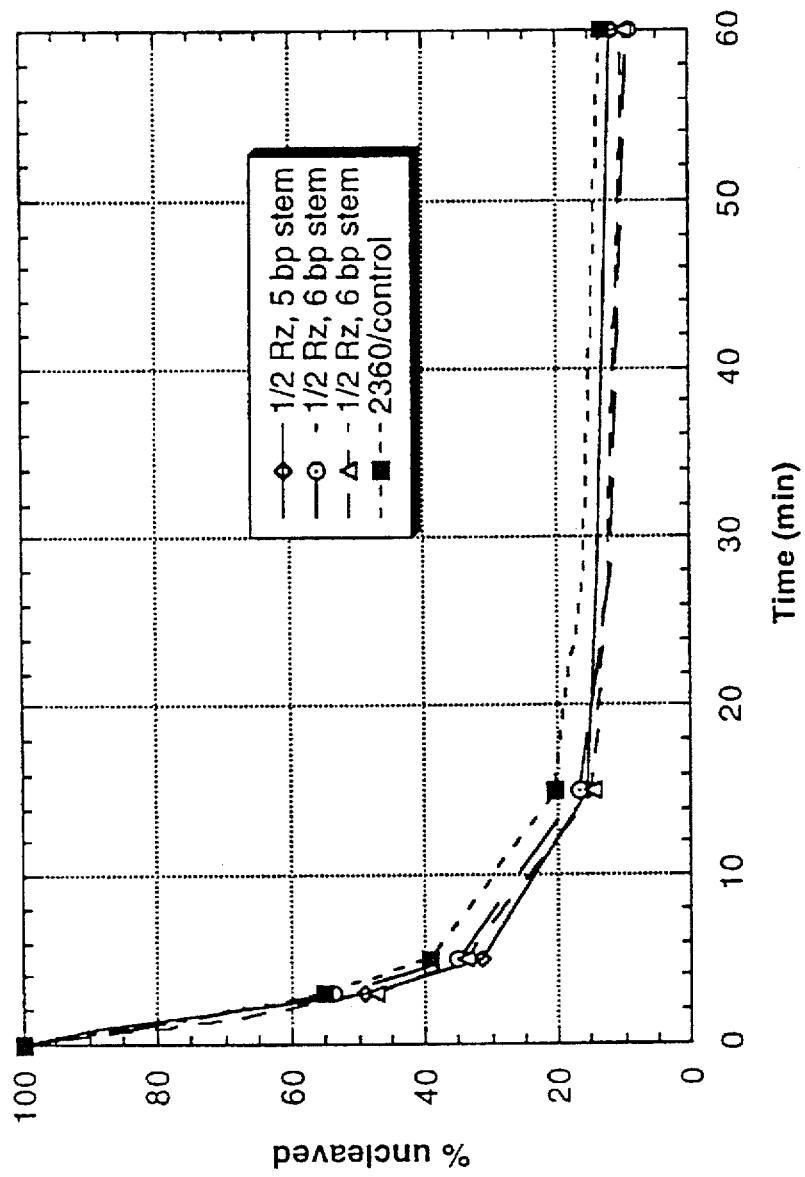

FIG. 10 shows comparative cleavage activity of half ribozymes, containing five and six base pair stem II regions, that are not covalently linked vs a full length ribozyme. Assays were carried out under ribozyme excess conditions.

Figure 11:
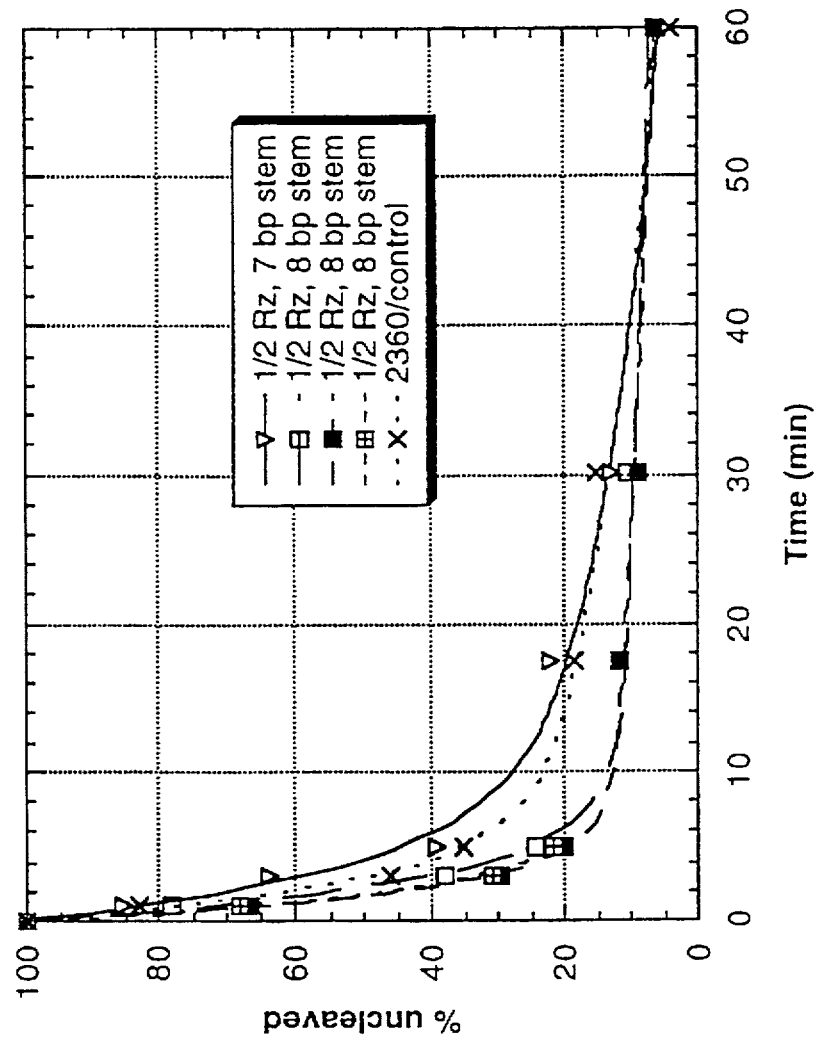

FIG. 11 shows comparative cleavage activity of half ribozymes, containing seven and eight base pair stem II regions, that are not covalently linked vs a full length ribozyme. Assays were carried out under ribozyme excess conditions.

Figure 12:
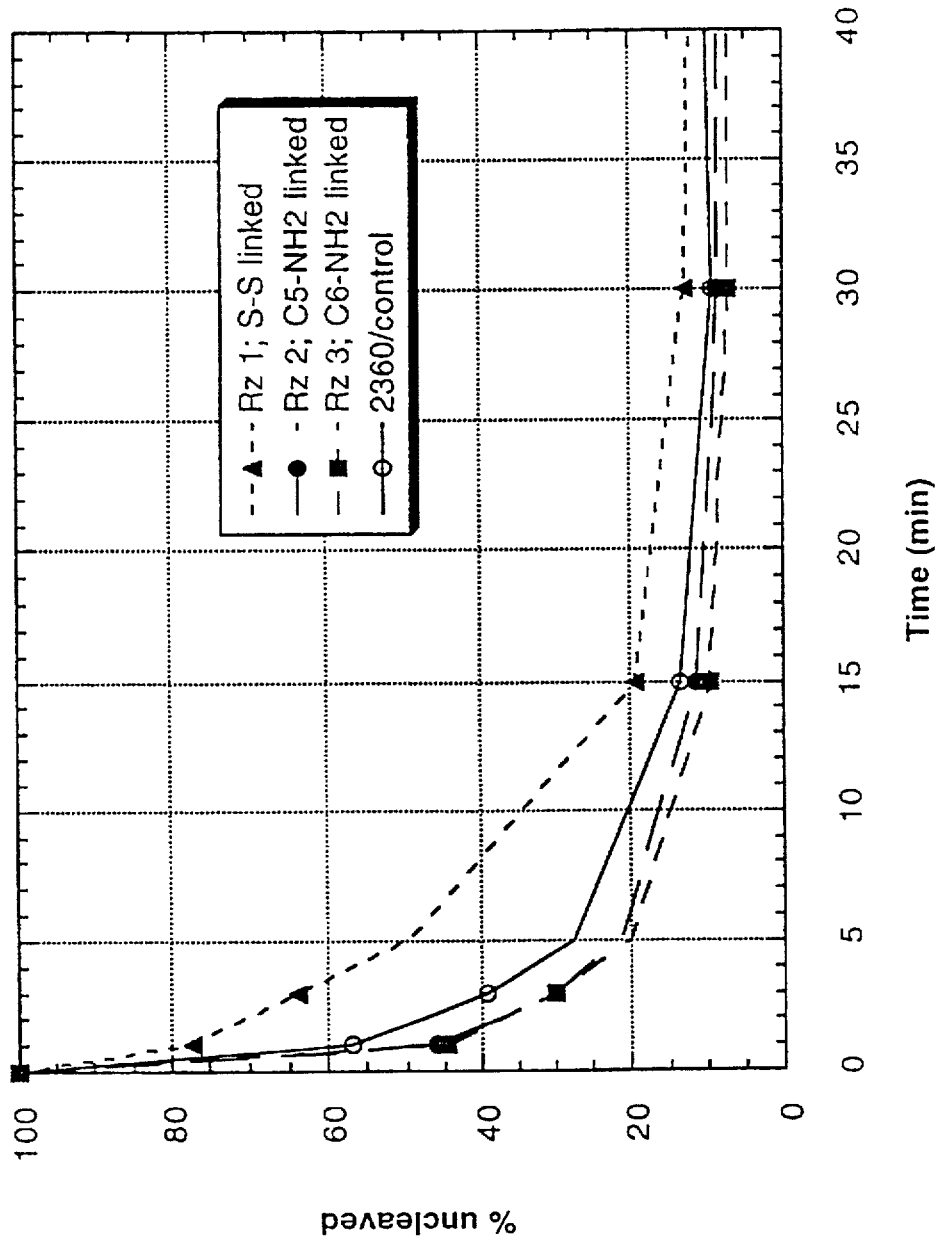

FIG. 12 shows comparative cleavage assay of Rz 1, 2 and 3 (see FIG. 9) formed from crosslinking reactions vs a full length ribozyme control. Assays were carried out under ribozyme excess conditions.

Figure 13:
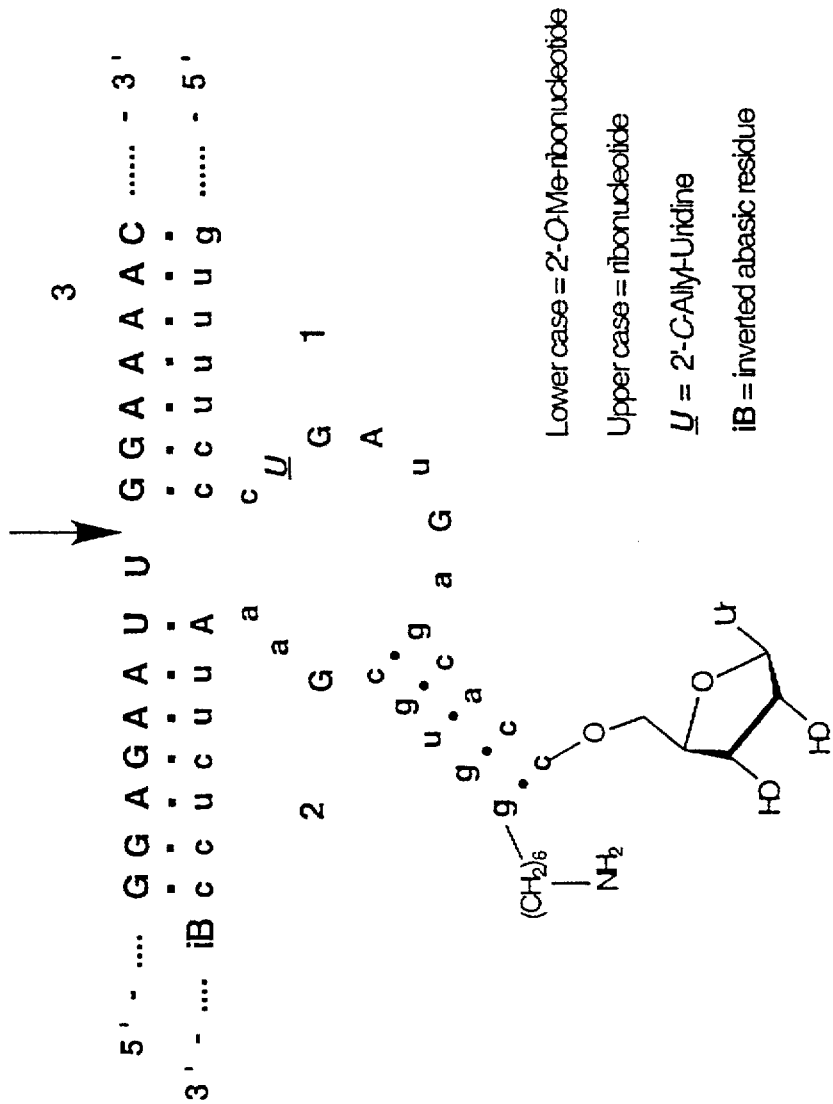

FIG. 13 is a diagrammatic representation of c-myb site 575 hammerhead half-ribozymes and substrate RNA. The arrow indicates the site of cleavage.

Figure 14A:
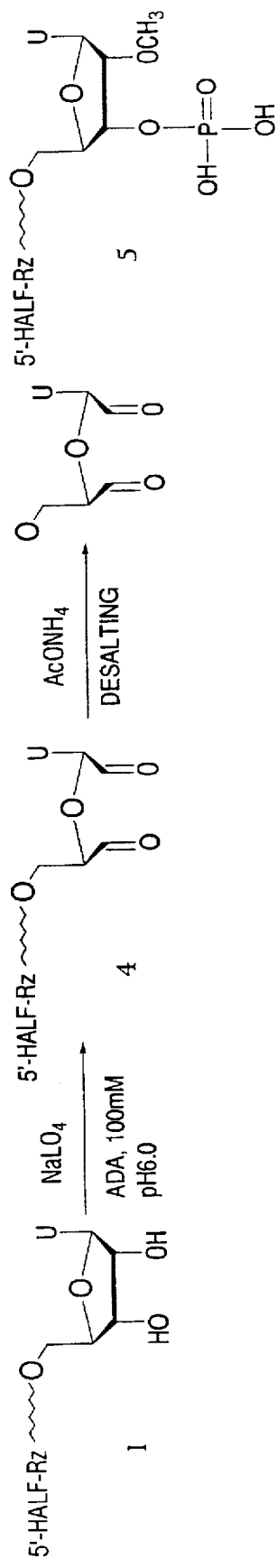

FIG. 14A) shows the synthesis of acyclic 2',3'-dialdehyde-5'-half-ribozyme (4) and 3'-phosphoryl-5'-half-ribozyme (5) from 3'-uridilyl-5'-half-ribozyme (1).

Figure 14C:
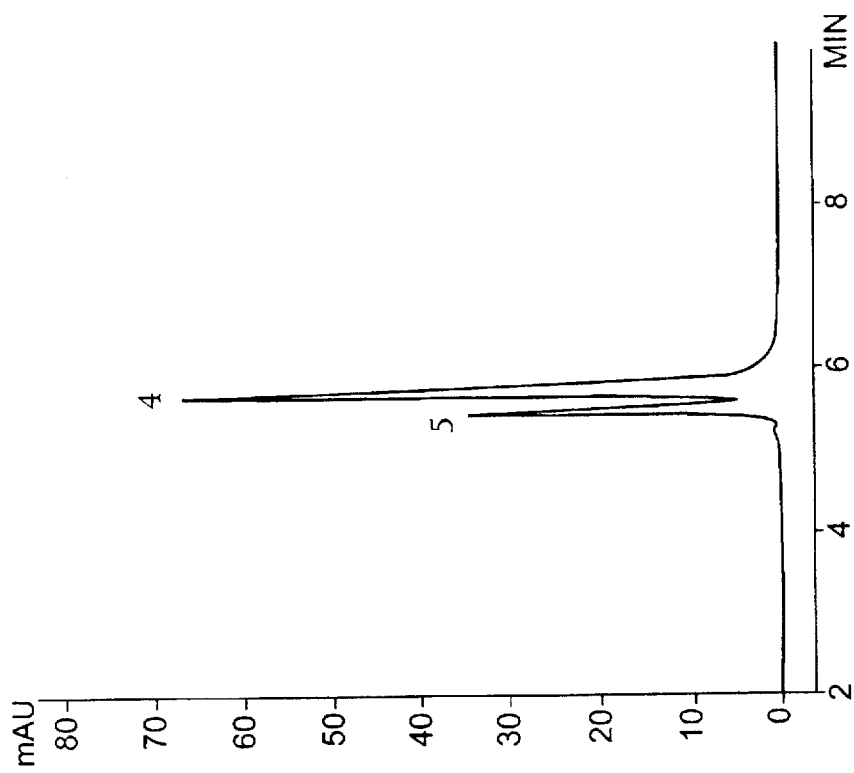
Figure 14B:
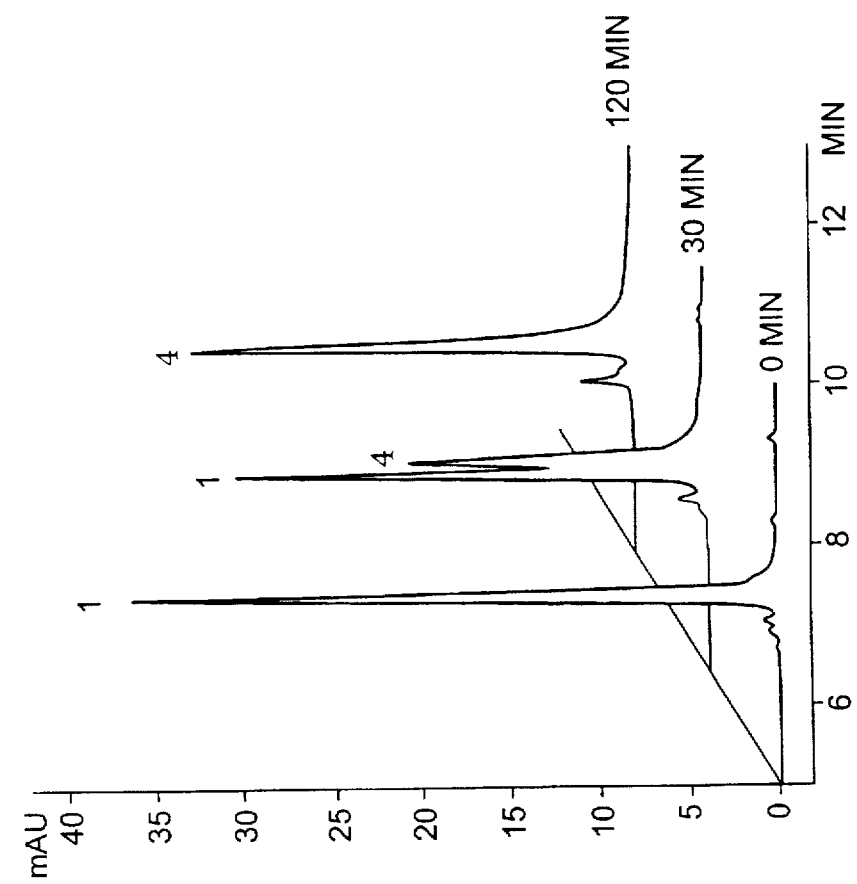

FIG. 14B) shows anion exchange HPLC analysis of reaction of 1 with $NaIO_4$ at room temperature.

FIG. 14C) shows the HPLC profile of ammonium acetate desalted compound 4.

Figure 15:
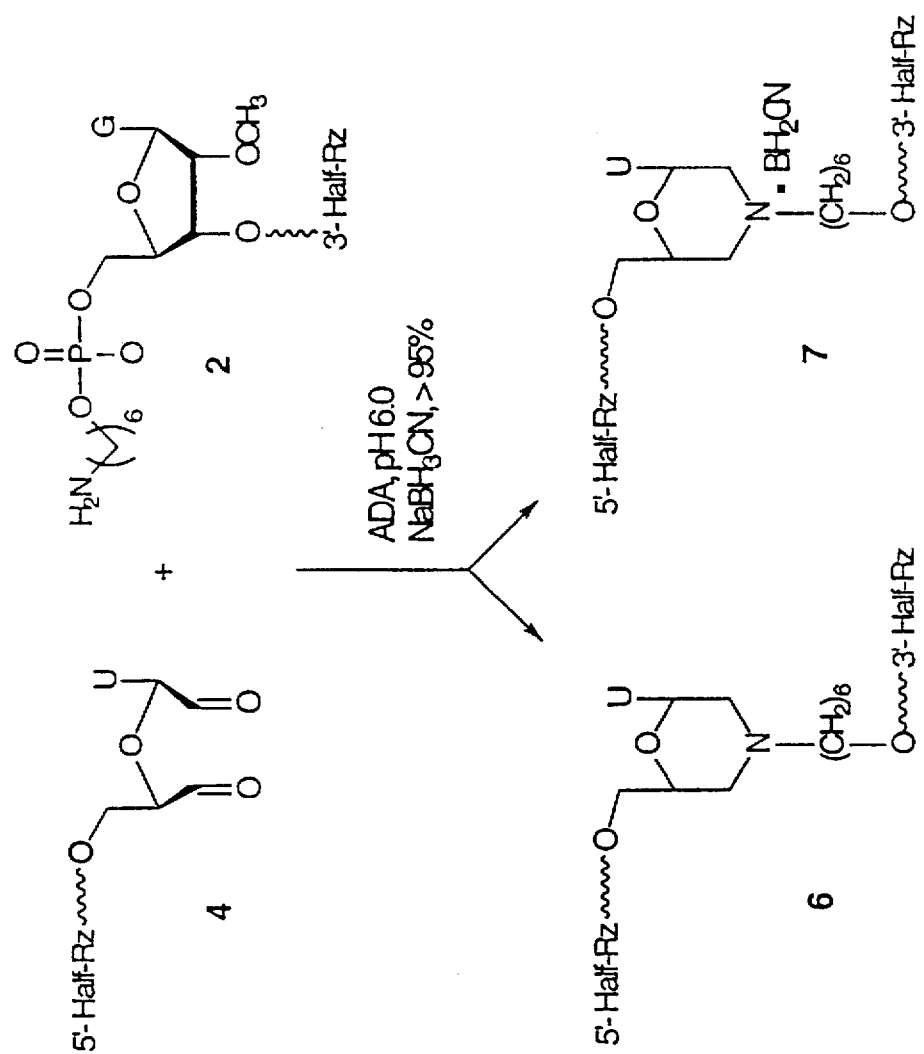

FIG. 15 is a schematic representation of synthesis of morpholino-linked ribozymes.

Figure 16:
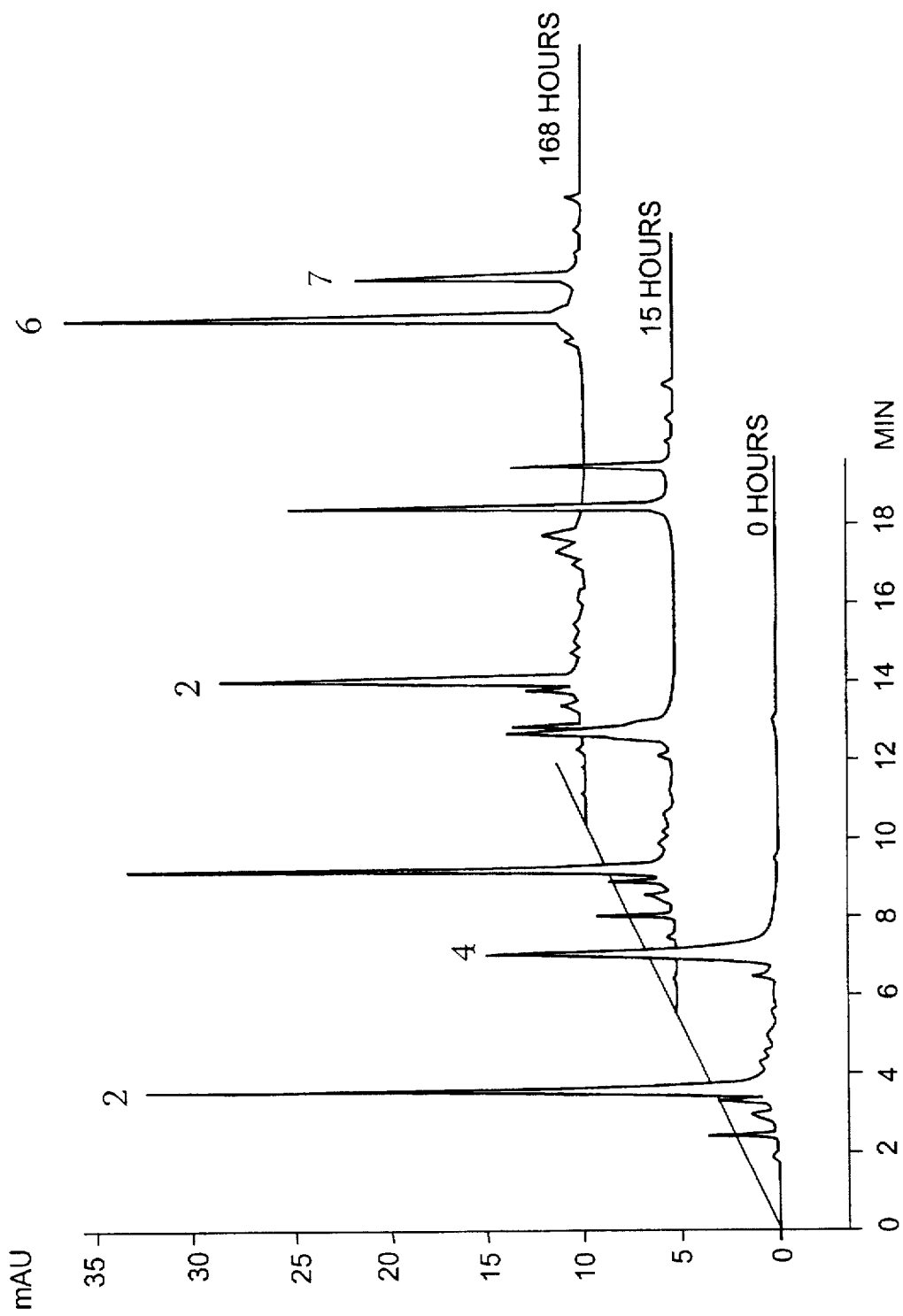

FIG. 16 shows an anion-exchange HPLC analysis of the reductive alkylation of compounds 2 and 4.

METHODS

The following are examples of preferred embodiments of the present invention. Those in the art will recognize that these are not limiting examples but rather are provided to guide those in the art to the full breadth of meaning of the present invention. Routine procedures can be used to utilize other coupling regions not exemplified below.

Ribozymes were synthesized in two parts and tested without ligation for catalytic activity. Referring to FIG. 10, the cleavage activity of the half ribozymes containing between 5 and 8 base pairs stem IIs at 40 nM under single turnover conditions was comparable to that of the full length oligomer as shown in FIGS. 11 and 12. The same half ribozymes were synthesized with suitable modifications at the nascent stem II loop to allow for crosslinking. The halves were purified and chemically ligated, using a variety of crosslinking methods. The resulting full length ribozymes (see FIG. 9) exhibited similar cleavage activity as the linearly synthesized full length oligomer as shown in FIG. 12.

Synthesis, Deprotection and Purification of RNA
Synthesis of RNA

The general procedures for RNA synthesis have been described previously (Usman et al., (1987) *J. Am. Chem. Soc.*, 109, 7845–7854 and Scaringe et al., supra; Wincott et al., 1995 *Nucleic Acids Res.* in press). Small scale syntheses were conducted on a 394 (ABI) synthesizer using a modified 2.5 µmol scale protocol with a 5 min coupling step for alkylsilyl protected nucleotides and 2.5 min coupling step for 2'-O-methylated nucleotides. Table II outlines the amounts, and the contact times, of the reagents used in the synthesis cycle. A 6.5-fold excess (163 µL of 0.1M=16.3 µmol) of phosphoramidite and a 24-fold excess (238 µL of 0.25M=59.5 µmol) relative to polymer-bound 5'-hydroxyl was used in each coupling cycle. Average coupling yields on the 394, determined by colorimetric quantitation of the trityl fractions, was 97.5–99%. Other oligonucleotide synthesis reagents for the 394: Detritylation solution was 2% TCA in methylene chloride (ABI); capping was performed with 16% N-Methyl imidazole in THF (ABI) and 10% acetic anhydride/10% 2,6-lutidine in THF (ABI); oxidation solution was 16.9 mM 12, 49 mM pyridine, 9% water in THF (Millipore). B & J Synthesis Grade acetonitrile was used directly from the reagent bottle. S-Ethyl tetrazole solution (0.25M in acetonitrile) was made up from the solid obtained from American International Chemical, Inc.

RNA Deprotection of Exocyclic Amino Protecting Groups Using Methylamine (MA)

The polymer-bound oligoribonucleotide, trityl-off, was transferred from the synthesis column to a 4 mL glass screw top vial and suspended in a solution of methylamine (MA) at 65° C. for 10 min. After cooling to -20° C., the supernatant was removed from the polymer support. The support was washed three times with 1.0 mL of EtOH:MeCN:H$_2$O/ 3:1:1, vortexed and the supernatant was then added to the first supernatant. The combined supernatants, containing the oligoribonucleotide, were dried to a white powder.

Trityl-off RNA Deprotection of 2'-Hydroxyl Alkylsilyl Protecting Groups Using Anhydrous TEA.3HF The base-deprotected oligoribonucleotide was resuspended in anhydrous TEA.HF/NMP solution (250 μL of a solution of 1.5 mL N-methylpyrrolidinone, 750 μL TEA and 1.0 mL TEA.3HF to provide a 1.4M HF concentration) and heated to 65° C. for 1.5 h. The resulting, fully deprotected, oligomer was quenched with 50 mM TEAB (9 mL) prior to anion exchange desalting.

For anion exchange desalting of the deprotected oligomer, the TEAB solution was loaded onto a Qiagen 500® anion exchange cartridge (Qiagen Inc.) that was prewashed with 50 mM TEAB (10 mL). After washing the loaded cartridge with 50 mM TEAB (10 mL), the RNA was eluted with 2M TEAB (10 mL) and dried down to a white powder (Scaringe et al., 1990 *Nucleic Acids Res.*, 18, 5433).

RNA Purification

For a small scale (2.5 μmol) synthesis, the crude material was diluted to 5 mL with RNase free water. The sample was injected onto either a Pharmacia Mono Q® 16/10 mm or Dionex NucleoPac® PA-100 22×250 mm column with 100% buffer A (10 mM NaClO$_4$). A gradient from 180–210 mM NaClO$_4$ at a rate of 8 mL/min for a Pharmacia Mono Q anion-exchange column or 100–150 mM NaClO$_4$ at a rate of 15 mL/min for a Dionex NucleoPac® anion-exchange column was used to elute the RNA. Fractions were analyzed by HPLC and those containing full length product ~80% by peak area were pooled for desalting. The pooled fractions were applied to a SepPak cartridge (C$_{18}$) that was prewashed successively with CH$_3$CN (10 mL), CH$_3$CN/MeOH/H$_2$O:1/ 1/1 (10 mL) and RNase free H$_2$O (20 mL). Following sample application, the cartridge was washed with RNase free H$_2$O (10 mL) to remove the salt. Product was then eluted from the column with CH$_3$CN/MeOH/H$_2$O:1/1/1 (10 mL) and dried.

Biochemical Activity

Ribozyme Activity Assay

Ribozymes and 5'-$^{32}$P-end-labeled substrate were heated separately in reaction buffer (50 mM Tris-Cl, pH 7.5; 10 mM MgCl$_2$) to 95° C. for 2 min, quenched on ice, and equilibrated to 37° C. prior to starting the reactions. Reactions were carried out in enzyme excess, and were started by mixing ~1 nM substrate and 40 nM ribozyme to a final volume of 50 μL. Aliquots of 5 μL were removed at 1, 5, 15, 30, 60 and 120 min, quenched in formamide loading buffer, and loaded onto 15% polyacrylamide/8M urea gels. The fraction of substrate and product present at each time point was determined by quantitation of scanned images from a Molecular Dynamics PhosphorImager®. Ribozyme cleavage rates were calculated from plots of the fraction of substrate remaining vs time using a double exponential curve fit (Kaleidagraph, Synergy Software).

EXAMPLE 1

Referring to FIG. 8 the 5' half of a hammerhead ribozyme was provided with a ribose group. This was oxidatively cleaved with NaIO$_4$ and reacted with the 3' half of the ribozyme having an amino group under reducing conditions. The resulting ribozyme consisted of the two half ribozyme linked by a morpholino group.

One equivalent of (200 micrograms) of RPI3631 (5' half hammerhead with a 3'OH) and 5 equivalents (1000 micrograms) of RPI3631 (3' half with 5' C5-NH$_2$) all with RPI 3635 (3' half hammerhead ribozyme with 5' C5-NH$_2$) were used in this reaction. The limiting oligonucleotide was oxidized first with 3.6 equivalents of sodium periodate for sixty minutes on ice in DEPC water quenched with 7.2 equivalents of ethylene glycol for 30 minutes on ice and the 5 equivalents of the amino oligo added. 0.5 Molar tricine buffer, pH 9, was added to provide 25 millimolar final tricine concentration and left for 30 minutes on ice. 50 equivalents of sodium cyanoborohydride was then added and the pH reduced to 6.5 with acetic acid and reaction left for 60 minutes on ice. The resulting full length ribozyme was then purified for further analysis.

EXAMPLE 2

Amide Bond

Referring again to FIG. 8 and 9, a 5' half of ribozyme was provided with a carboxyl group at its 2' position and was coupled with an amine containing 3' half ribozyme. The provision of a coupling reagent resulted in a full-length ribozyme having an amide bond.

EXAMPLE 3

Disulfide Bond

Referring to FIG. 8 and 9, 250 micrograms of RPI3881 and 250 micrograms of RPI3636 half ribozyme were separately deprotected with dithiothreitol overnight at 37° C. They were mixed together at 1:1 mole ratio in a 100 mM sodium phosphate buffer at pH 8 and 4M copper sulfate and 0.8 mM 1,10-phenanthroline (final concentrations) was added for two hours at room temperature (20°–25° C.) and the resulting mixture gel purified. The overall purification yield of full length ribozyme was 30%.

EXAMPLE 4

Synthesis And Activity Of Morpholino-Linked Ribozymes

Analogs of RPI.2972 (Table III) were synthesized as described above. RPI.2972 is a chemically stabilized ribozyme targeted against site 575 of c-myb mRNA that inhibits smooth muscle cell proliferation with an IC$_{50}$ of approximately 75 nM (Stinchcomb et al., International PCT Publication No. WO 95/31541. Referring to FIG. 13, the half-ribozymes, 1 and 2, used in this study contained a modified 5 base-paired stem II and the appropriate reactive groups at the termini.

Half-ribozymes 1 and 2 were synthesized and purified according standard methods. The 3'-uridilyl-5'-half-ribozyme, 1, (150 μM) was dissolved in sodium N$_2$-acetamido-2-imino-diacetate (ADA) buffer (100 mM, pH 6.0) and subjected to oxidative cleavage with 2 molar equivalents of a 100 mM aqueous solution of sodium periodate (FIG. 14A). After 2 h, the acyclic 2',3'-dialdehyde derivative 4 was formed quantitatively, as confirmed by HPLC monitoring (FIG. 14B). ES-MS analysis, performed on purified 1 (calc. 6490.2, found 6489.1) and 4 (calc.

6488.2, found 6489.2), did not allow direct identification since 1 and 4 differed only by two atomic mass units (amu). However, the presence of the 3'-phosphoryl-5'-half-ribozyme, 5, (calc. 6263.1, found 6262.6) in the ES-mass spectrum of 4 provided supportive evidence. Indeed, 5 confirmed the dialdehydic structure of 4 since it resulted from the $E_2$-elimination of 2',3'-dideoxy-2',3'-diformyl-5'-deoxy-5'-methyleneuridine occurring during the ammonium acetate precipitation of 4 (FIG. 14A). As expected, 5 (retention time=5.3 min) was never observed in non-desalted samples of 4 (retention time=5.5 min) (FIG. 14C) thus corroborating that the ammonium acetate pH 8 precipitation was responsible for the base-catalyzed β-elimination.

The crude, oxidized mixture containing 4 and an excess of $NaIO_4$ was then directly mixed with the 5'-aminohexyl-3'-half-ribozyme 2 under reductive amination conditions (FIG. 15). The unreacted sodium periodate was not quenched with a cis-diol source as the resulting aldehydes might have competed with 4 in the reductive alkylation reaction of 2. Moreover, since the 3'-end of 2 contained an inverted abasic residue, no cis-diol functionalities susceptible to undesired oxidative cleavage were present. Typically, 2 (600 μM) was added to the crude 4 in 100 mM ADA buffer pH 6.0. The transient Schiff base adduct could not be formed unless a 5 molar excess of aqueous $NaBH_3CN$ (500 mM) was introduced (FIG. 15) leading to the concomitant formation of the cross-linked products 6 and 7 in a 3 to 1 ratio. Reducing the molar excess of 2 from 4 eq. to nearly stoichiometric (1.5 eq.) did not change the course of the reaction. After purification, 6 was identified as the morpholino-linked ribozyme on the basis of ES-MS analysis (calc. 11723.7, found 11724.8). Interestingly, the ES-MS of compound 7 exhibited a mass signal higher than 6 by 38.8 amu (FIG. 16). This suggested that the higher mass product 7 was a cyanoborane adduct of the tertiary nitrogen atom of the morpholino moiety (calc. 11762.7, found 11763.6). To confirm the identity of compound 7, applicant prepared $^{13}C$-labeled $NaBH_3^{13}CN$ from $Na^{13}CN$ according to the procedure of Hui (*Inorg. Chem.* 1980, 19, 3185–3186). and repeated the reductive amination of 4 on a 2 μmol scale. As expected, 6 and 7 were produced, $^{13}C$-NMR performed on the two products clearly showed a singlet at 126.8 ppm for 7, confirming the presence of a cyanoborane adduct whereas this signal could not be observed in the $^{13}C$ spectrum of 6.

Once the morpholino-linked ribozymes were synthesized and characterized it was critical to ascertain the effect of this chemical cross-link on the rate of catalytic cleavage. Ribozymes 6 and 7 as well as the control RPI.2972 were assayed for their cleavage rate on short substrate 3 (FIG. 13) as described above. The cleavage activity of the morpholino-linked ribozyme 6 was very similar to that of the control (Table III), confirming that one can extensively modify the loop II/stem II region without hampering catalytic efficiency. Interestingly, 7 cleaved substrate 3 six times faster than the control, RPI.2972.

This general segmented assembly can be readily used to synthesize and assemble larger ribozyme motifs such as hairpin, Hepatitis Delta Virus or VS ribozymes.

Other embodiments are within the following claims.

TABLE 1

Characteristics of Ribozymes

Group I Introns

Size: ~150 to >1000 nucleotides.
Requires a U in the target sequence immediately 5' of the cleavage site.

TABLE 1-continued

Characteristics of Ribozymes

Binds 4–6 nucleotides at 5' side of cleavage site.
Over 75 known members of this class. Found in *Tetrahymena thermophila* rRNA, fungal mitochondria, chloroplasts, phage T4, blue-green algae, and others.
RNase P RNA (M1 RNA)

Figure 1:
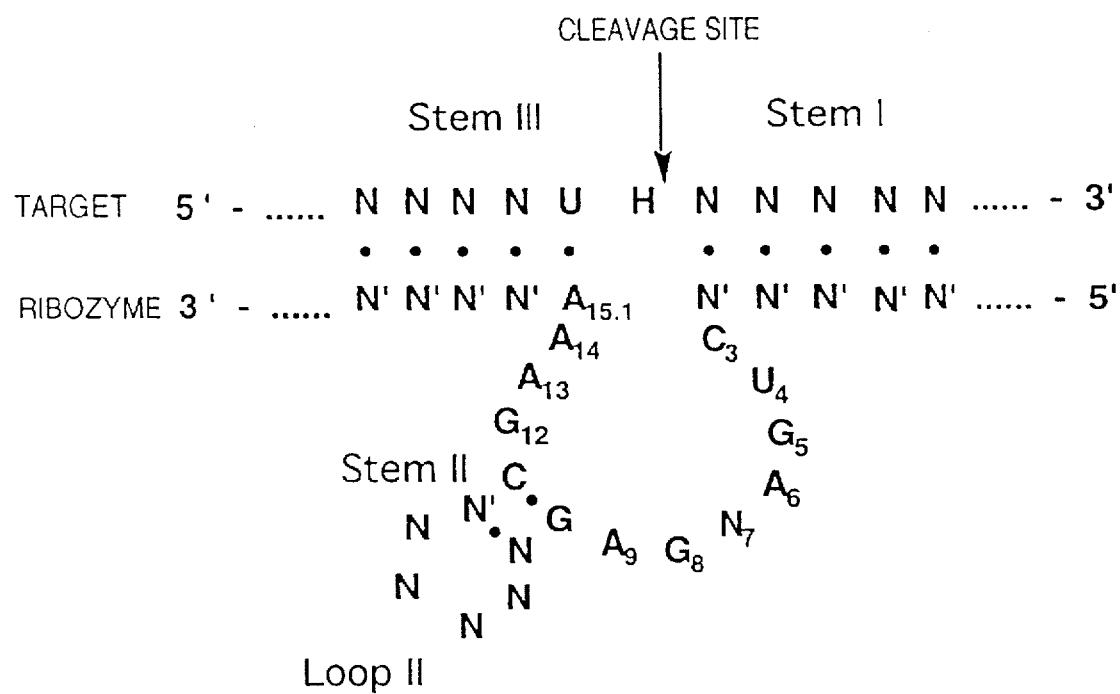

Size: ~290 to 400 nucleotides.
RNA portion of a ribonucleoprotein enzyme. Cleaves tRNA precursors to form mature tRNA.
Roughly 10 known members of this group all are bacterial in origin.
Hammerhead (HH) Ribozyme Size: ~13 to 40 nucleotides.
Requires the target sequence UH immediately 5' of the cleavage site.
Binds a variable number of nucleotides on both sides of the cleavage site.
14 known members of this class. Found in a number of plant pathogens (virusoids) that use RNA as the infectious agent (Figure 1 and 2).
Hairpin (HP) Ribozyme Size: ~50 nucleotides.
Prefers the target sequence GUC immediately 3' of the cleavage site.
Binds 4–6 nucleotides at 5' side of the cleavage site and a variable number to the 3' side of the cleavage site.
Only 3 known member of this class. Found in three plant pathogen (satellite RNAs of the tobacco ringspot virus, arabis mosaic virus and chicory yellow mottle virus) which uses RNA as the infectious agent (Figure 3).
Hepatitis Delta Virus (HDV) Ribozyme Size: 50–60 nucleotides (at present).
Sequence requirements not fully determined.
Binding sites and structural requirements not fully determined, although no sequences 5' of cleavage site are required.
Only 1 known member of this class. Found in human HDV (Figure 4).
Neurospora VS RNA (VS) Ribozyme Size: ~144 nucleotides (at present)
Cleavage of target RNAs recently demonstrated.
Sequence requirements not fully determined.
Binding sites and structural requirements not fully determined. Only 1 known member of this class. Found in Neurospora VS RNA (Figure 5).

TABLE II 2.5 μmol Synthesis Cycle

| Reagent | Equivalents | Amount | Wait Time* |
|---|---|---|---|
| Phosphoramidites | 6.5 | 163 μL | 2.5/5 min |
| S-Ethyl Tetrazole | 23.8 | 238 μL | 2.5/5 min |
| Acetic Anhydride | 100 | 233 μL | 5 sec |
| N-Methyl Imidazole | 186 | 233 μL | 5 sec |
| TCA | 83.2 | 1.73 mL | 21 sec |
| Iodine | 8.0 | 1.18 mL | 45 sec |
| Acetonitrile | NA | 6.67 mL | NA |

*Wait time does not include contact time during delivery. Where two coupling times are indicated the first refers to RNA coupling and the second to 2'-O-methyl coupling.

TABLE III

Cleavage rate of the substrate 3 by the ribozymes 6, 7 and RPI.2972.

| Ribozyme | 6 | 7 | RPI 2972[b] |
|---|---|---|---|
| $k_{obs}$ (min$^{-1}$)[a] | 0.013 | 0.145 | 0.023 |

[a] [Rz] = 500 nM, [3] ~ 1 nM, 50 nM tris.HCl pH 8.0, 25° C., 40 nM $Mg^{++}$.
[b] g,u,u,u,uc ccU Gau Gag gcc gaa agg ccG aaA uuc ucc iB

We claim:

1. A method for synthesis of an enzymatic nucleic acid molecule, comprising the steps of:
providing a 3' and a 5' portion of said enzymatic nucleic acid having independent chemically reactive groups at the 5' and 3' positions, respectively, under conditions in which a covalent bond is formed between said 3' and 5' portions by said chemically reactive groups, said bond being selected from the group consisting of, disulfide, morpholino, amide, ether, thioether, amine, a double bond, sulfonamide, ester, carbonate, hydrazone, said bond not being a natural bond formed between a 5' phosphate group and a 3' hydroxyl group.

2. The method of claim 1, wherein said nucleic acid molecule has a hammerhead motif with a stem II region and said 3' and 5' positions each have said chemically reactive groups in or immediately adjacent to the stem II region.

3. The method of claim 1, wherein one said chemically reactive group has the formula $(CH_2)_nSH$ and the other chemically reactive group has the formula $(CH_2)_nSH$, wherein each n independently is an integer from 0 to 10 inclusive and may be the same or different.

4. The method of claim 1, wherein one said chemically reactive group has the formula $(CH_2)_nNH_2$ and the other chemically reactive group is a ribose, wherein n is an integer from 0 to 10 inclusive.

5. The method of claim 1, wherein one said chemically reactive group has the formula $(CH_2)_nNH_2$ and the other chemically reactive group is COOH, wherein n is an integer from 0 to 10 inclusive.

6. The method of claim 1, wherein one said chemically reactive group has the formula $(CH_2)_nX$ and the other chemically reactive group has the formula $(CH_2)_nOH$ or $(CH_2)_nSH$; wherein each n independently is an integer from 0 to 10 inclusive and may be the same or different; X is a halogen.

7. The method of claim 1, wherein one said chemically reactive group has the formula $(CH_2)_nNH_2$ and the other chemically reactive group is CHO, wherein n is an integer from 0 to 10 inclusive.

8. The method of claim 1, wherein one said chemically reactive group has the formula $(CH_2)_nPPh_3$ and the other chemically reactive group is CHO, wherein n is an integer from 0 to 10 inclusive.

9. The method of claim 1, wherein one said chemically reactive group has the formula $(CH_2)_nNH_2$ and the other chemically reactive group has the formula $(CH_2)_nSO_2Cl$, wherein each n independently is an integer from 0 to 10 inclusive and may be the same or different.

10. The method of claim 1, wherein one said chemically reactive group has the formula $(CH_2)_nOH$ and the other chemically reactive group is COOH, wherein n is an integer from 0 to 10 inclusive.

11. The method of claim 1, wherein one said chemically reactive group has the formula $(CH_2)_nCOH$ and the other chemically reactive group has the formula $(CH_2)_nNH_2$, wherein each n independently is an integer from 0 to 10 inclusive and may be the same or different.

12. The method of claim 1, wherein one said chemically reactive group has the formula $(CH_2)_nCOX$ and the other chemically reactive group has the formula $(CH_2)_nOH$, wherein each n independently is an integer from 0 to 10 inclusive and may be the same or different; X is a halogen.

13. The method of claim 5, wherein said conditions include the provision of a coupling reagent.

* * * * *